United States Patent
Isaac et al.

(10) Patent No.: US 10,997,561 B2
(45) Date of Patent: May 4, 2021

(54) PROVIDER COMPENSATION MANAGEMENT AND ADMINISTRATION SYSTEM

(71) Applicant: Hallmark Healthcare Solutions, LLC, Hauppauge, NY (US)

(72) Inventors: Neeraj Isaac, Florence, NJ (US); Isaac Ullatil, Florence, NJ (US)

(73) Assignee: HALLMARK HEALTHCARE SOLUTIONS, INC., Hauppauge, NY (US)

( * ) Notice: Subject to any disclaimer, the term of this patent is extended or adjusted under 35 U.S.C. 154(b) by 162 days.

(21) Appl. No.: 15/840,042

(22) Filed: Dec. 13, 2017

(65) Prior Publication Data

US 2019/0180247 A1 Jun. 13, 2019

(51) Int. Cl.
*G06Q 10/10* (2012.01)
*G06Q 10/06* (2012.01)
*G06Q 30/02* (2012.01)
*G16H 40/00* (2018.01)

(52) U.S. Cl.
CPC ....... *G06Q 10/1057* (2013.01); *G06Q 10/067* (2013.01); *G06Q 10/06393* (2013.01); *G06Q 30/0203* (2013.01); *G16H 40/00* (2018.01)

(58) Field of Classification Search
CPC ......... G06Q 10/1057; G06Q 10/06393; G06Q 10/067; G06Q 30/0203; G16H 40/00; G16H 40/20
See application file for complete search history.

(56) References Cited

U.S. PATENT DOCUMENTS 5,819,231 A * 10/1998 Tremaine ......... G06Q 10/06375
                                                    705/7.21
7,805,354 B2 * 9/2010 Coleman .............. G06Q 10/105
                                                    705/37
8,204,809 B1 * 6/2012 Wise ..................... G06Q 40/06
                                                    705/35

(Continued)

OTHER PUBLICATIONS

An empirical analysis of continuing improvements following the implementation of a performance-based compensation plan RD Banker, SY Lee, G Potter, D Srinivasan—Journal of Accounting and . . . , 2000—Elsevier (Year: 2000).*

(Continued)

*Primary Examiner* — Jonathan G Sterrett
(74) *Attorney, Agent, or Firm* — Gearhart Law LLC; David Postolski, Esq.

(57) ABSTRACT

Disclosed embodiments provide techniques that alleviate the challenges healthcare leaders face in the administration and management of provider compensation. Disclosed embodiments provide systems and methods that automate calculating and adjudicating, and monitoring provider compensation while providing real-time feedback to administrators and providers on performance under the compensation methodology. The automation allows organizations to increase transparency while providing secure access to information, allowing for more robust discussion of alternatives and alignment between the enterprise and providers. Thus, disclosed embodiments serve to ensure compliance, enable transparency, and empower validation throughout the provider compensation process.

20 Claims, 8 Drawing Sheets

(56) References Cited

U.S. PATENT DOCUMENTS

| | | | | |
|---|---|---|---|---|
| 8,311,863 B1* | 11/2012 | Kemp | ................ | G06Q 10/0639 |
| | | | | 705/7.11 |
| 8,355,926 B1* | 1/2013 | Hinz | ..................... | G16H 40/20 |
| | | | | 705/2 |
| 2002/0029177 A1* | 3/2002 | Smisek | ................ | G06Q 30/02 |
| | | | | 705/30 |
| 2002/0035506 A1* | 3/2002 | Loya | ..................... | G06Q 10/06 |
| | | | | 705/14.19 |
| 2003/0229522 A1* | 12/2003 | Thompson | ........... | G06Q 10/067 |
| | | | | 705/4 |
| 2005/0182660 A1* | 8/2005 | Henley | ................ | G06F 19/328 |
| | | | | 705/2 |
| 2005/0192823 A1* | 9/2005 | Kuhn | ................ | G06Q 10/0639 |
| | | | | 705/7.42 |
| 2007/0027714 A1* | 2/2007 | Fenno | .................... | G06Q 10/06 |
| | | | | 705/2 |
| 2007/0094110 A1* | 4/2007 | McCrea | ................ | G06Q 30/04 |
| | | | | 705/32 |
| 2007/0156551 A1* | 7/2007 | Smith | .................... | G06Q 40/00 |
| | | | | 705/35 |
| 2008/0065467 A1* | 3/2008 | Nyegaard | .............. | G06Q 10/00 |
| | | | | 705/7.32 |
| 2011/0022479 A1* | 1/2011 | Henley | ................. | G06F 19/328 |
| | | | | 705/14.73 |
| 2014/0081652 A1* | 3/2014 | Klindworth | ............ | G06Q 10/10 |
| | | | | 705/2 |
| 2014/0324645 A1* | 10/2014 | Stiffler | ................... | G06Q 40/12 |
| | | | | 705/30 |

OTHER PUBLICATIONS

Heisenberg II Features, retrieved from the web on Oct. 14, 2016 fromhttp://web.archive.org/web/20161014001029/http://www.heisenbergii.com/features.php (Year: 2016).*

Heisenberg II Product Sheet, retrieved from the web on Mar. 27, 2016 http://web.archive.org/web/20160327011337/http://heisenbergii.com/downloads/heisenberg2-product-sheet.pdf (Year: 2016).*

Payment systems and workplace industrial relations in Australian manufacturing industry: an historical overview C Wright—1990—ses.library.usyd.edu.au (Year: 1990).*

* cited by examiner

Physician Name: Jao Martinez — 802

Specialty: Obstetrics — 804

Contract Duration: 01/01/2018 - 12/31/2018 — 806

Projected RVUs: 6812 — 808

Projected Collections: 789251.32 — 810

Pay Elements

812

- ☑ Base Salary
- ○ Call Coverage Pay
- ○ Draw Against Productivity
- ☑ Hard to Fill Incentive Pay
- ○ Holiday Pay
- ○ Hospitalist Pay
- ○ Medical Directorship Pay
- ○ Meeting Pay

- ○ Moonlighting Pay
- ☑ Relocation Pay
- ○ Sign on Bonus Pay
- ○ Slow Shift Pay
- ○ Straight Productivity
- ☑ Supervision Pay
- ○ Training Pay

PROVIDER COMPENSATION MANAGEMENT AND ADMINISTRATION SYSTEM

FIELD

The present invention relates generally to administrative systems, and more particularly to a provider compensation management system.

BACKGROUND

Healthcare provider administration can be an extremely complex task. There are many important policy, regulatory, and legal details that must be tracked in order to properly acquire a new provider into a firm. This process is referred to as "onboarding." Details for onboarding can include verification and confirmation, medical licenses, malpractice insurance applications, controlled substance certificates, and more.

For the purposes of this disclosure, a provider is a physician or Advanced Practice Provider (APP), which includes Nurse Practitioners, and/or Physician Assistants. Provider compensation is another aspect of provider administration that can be quite complex. There are a variety of different compensation models that may be used for providers. For the purposes of this disclosure, a compensation model is a set of criteria to determine payment to providers. As examples, compensation models can include an equal salary model. In this model, the profits of the practice are distributed equally to all providers, regardless of their individual contributions to the revenues of the practice. Another possible provider compensation model is a productivity model. In this model, the provider compensation is based on work relative value unit (wRVU) productivity. In some variations of this model, there is a base salary for providers, with a portion of the total compensation based on the provider's own productivity, patient volume, or other metrics based on the activities they perform. Yet another compensation model is the straight salary model. This model features a fixed payment, typically disbursed monthly, pay period wise or bimonthly. Yet another compensation model is a salary plus productivity bonus model. This model provides a base salary plus a productivity bonus. The productivity bonus may be based on a variety of factors. One commonly applied metric is the work relative value unit (wRVU). An wRVU is applied to the various Current Procedural Terminology® (CPT) codes used to describe and bill professional services. Yet another compensation model is a salary plus incentive model. In this model, other factors are used to determine the provider bonus. These factors can include peer review, patient satisfaction, and/or the results of participation in quality programs such as the Provider Quality Reporting System (PQRS). The aforementioned compensation models are exemplary, and other models are possible. Some compensation models may be combinations of the aforementioned models. Thus, properly computing an appropriate provider compensation can be a challenging task.

Provider administration is an integral, but often underappreciated aspect of the health care system. It enables hospitals and medical practices to acquire and retain top medical talent, while also playing an important role in the management of health care costs. The task is challenging due to the many legal, regulatory, and policy factors that can impact provider administration. It is therefore desirable to have improvements in provider administration to provide enhanced efficiency, automation and reliability for these processes.

SUMMARY

In one embodiment, there is provided a computer-implemented method for provider compensation management and administration, comprising: obtaining contract terms; obtaining payment rules; obtaining compensation factors; and generating a compensation plan based on the obtained contract terms, payment rules, and compensation factors.

In another embodiment, obtaining compensation factors includes obtaining a provider region.

In another embodiment, obtaining compensation factors includes obtaining a provider specialty.

In another embodiment, obtaining compensation factors includes obtaining a provider pay grade table.

In another embodiment, the method further includes computation of fixed provider compensation and variable provider compensation.

In another embodiment, the method further includes performing a full-time equivalency (FTE) reconciliation.

In another embodiment, the method further includes reconciling contracted and actual pay amounts.

In another embodiment, the method further includes performing a calculation of fair market value.

In another embodiment, the method further includes adjusting provider compensation based on comparison of performance measured data with industry-standard data sets.

In another embodiment, the performance measured data includes one or more FTE classification categories.

In another embodiment, the performance measured data includes a benchmarking comparison.

In another embodiment, the performance measured data includes a quality component.

In another embodiment, generating a compensation plan further comprises incorporating, maximum payment rules, key industry measures and standards, client-specific key performance indicators and discreet pay element level details.

In another embodiment, the method further includes comparing a provider compensation to the calculated fair market value; and generating an alert in response to detecting a discrepancy exceeding a predetermined threshold.

In another embodiment, the method further includes generating a completed contractual document for a provider based on template and provider profile information.

In another embodiment, the method further includes performing workflow automation.

In another embodiment, the method further includes modeling provider compensation utilizing a plurality of compensation models; and providing an indication of compensation plan effectiveness for each model of the plurality of compensation models.

In another embodiment, generating a compensation plan includes providing compensation data serving as a single data source.

In another embodiment, the method further includes automating survey data collection.

In another embodiment, the method further includes using survey data to derive benchmarking data.

In another embodiment, there is provided an electronic computing device comprising: a processor; a memory coupled to the processor, the memory containing instructions, that when executed by the processor, perform the steps of: obtaining contract terms; obtaining payment rules;

obtaining compensation factors; and generating a compensation plan based on the obtained contract terms, payment rules, and compensation factors.

In another embodiment, the memory further comprises instructions, that when executed by the processor, perform the steps of obtaining compensation factors including a provider region.

In another embodiment, the memory further comprises instructions, that when executed by the processor, perform the steps of obtaining compensation factors including a provider specialty.

In another embodiment, the memory further comprises instructions, that when executed by the processor, perform the step of obtaining compensation factors including a provider pay grade table.

In another embodiment, the memory further comprises instructions, that when executed by the processor, perform the step of computing fixed provider compensation and variable provider compensation.

In another embodiment, the memory further comprises instructions, that when executed by the processor, perform the step of tracking expiration of malpractice insurance.

In another embodiment, the memory further comprises instructions, that when executed by the processor, perform the step of reconciling contracted and actual pay amounts.

In another embodiment, the memory further comprises instructions, that when executed by the processor, perform the step of performing a calculation of fair market value In another embodiment, the memory further comprises instructions, that when executed by the processor, perform the steps of: comparing a provider compensation to the calculated fair market value; and generating an alert in response to detecting a discrepancy exceeding a predetermined threshold.

In another embodiment, there is provided a computer program product for provider administration, for an electronic computing device comprising a computer readable storage medium having program instructions embodied therewith, the program instructions executable by a processor to cause the electronic computing device to: obtain contract terms; obtain payment rules; obtain compensation factors; and generate a compensation plan based on the obtained contract terms, payment rules, and compensation factors.

In yet another embodiment, the computer program product further comprises program instructions executable by a processor to cause the electronic computing device to: perform a calculation of fair market value; compare a provider compensation to the calculated fair market value; and generate an alert in response to detecting a discrepancy between the provider compensation and calculated fair market value that exceeds a predetermined threshold.

BRIEF DESCRIPTION OF THE DRAWINGS

FIG. 8 is an exemplary user interface in accordance with embodiments of the present invention.

Figure 1:
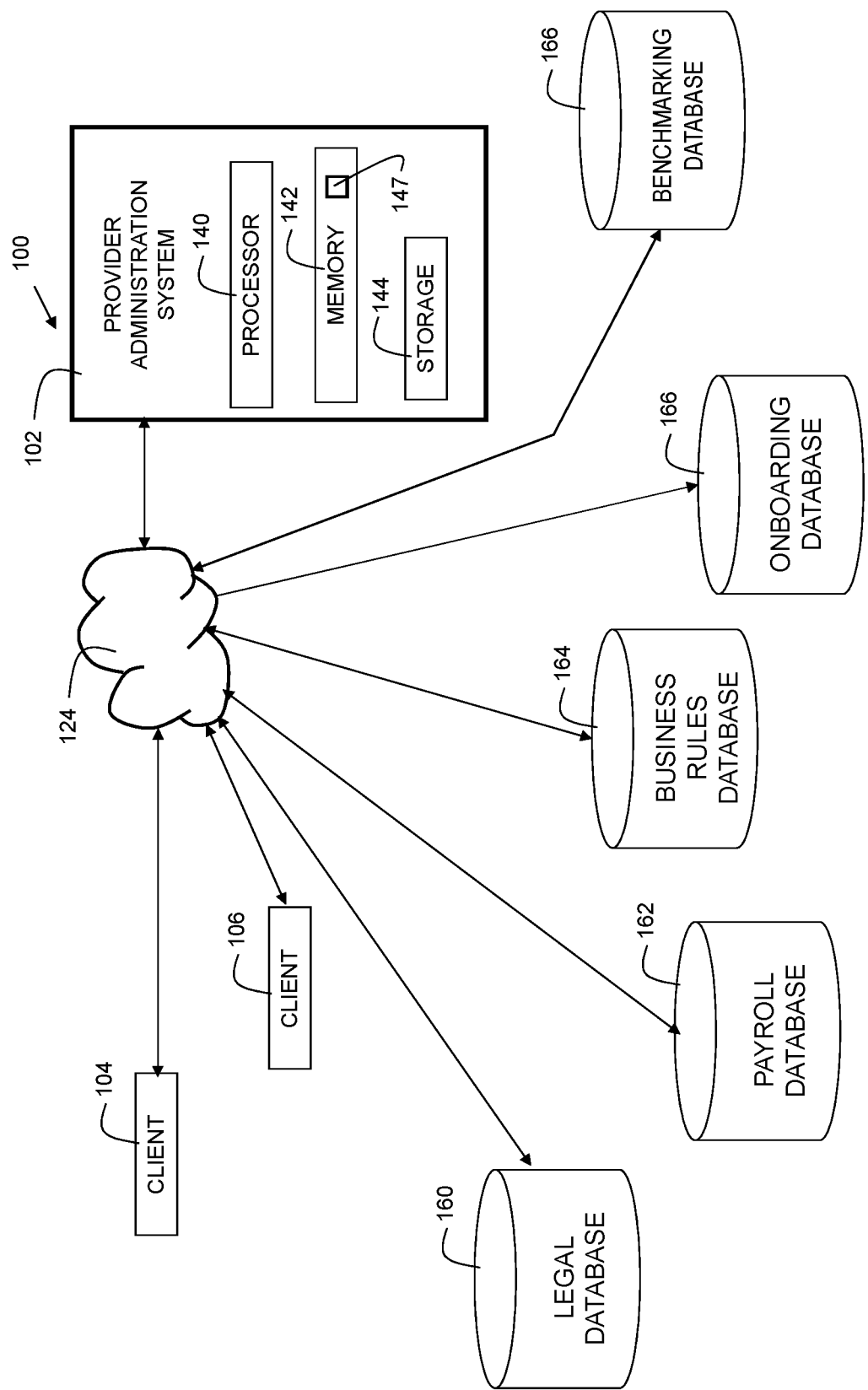
FIG. 1 depicts a system in accordance with embodiments of the present invention.

The structure, operation, and advantages of disclosed embodiments will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity.

DETAILED DESCRIPTION

In recent years, healthcare organizations have been struggling to develop, administer and adjudicate compensation plans using disconnected, labor-intensive processes and inadequate software. Furthermore, there is a compelling need among provider enterprises to more efficiently track and measure the success of their provider compensation plans against organizational goals and objectives. It is desirable to enable provider leaders to focus more on leading their organizations and less on the administrative components of their position. Disclosed embodiments provide techniques that alleviate the challenges healthcare leaders face in the administration and management of provider compensation. Disclosed embodiments provide systems and methods that automate calculating and adjudicating, and monitoring provider compensation while providing real-time feedback to enterprise users, administrators and providers on performance under the compensation methodology. The automation allows organizations to increase transparency while providing secure access to information, allowing for more robust discussion of alternatives and alignment between the enterprise and providers.

As more and more organizations are formally aligning with providers, large support structures are required to manage their provider organizations. Until now, provider compensation has been developed and administered through manual processes and tools. These tools limit organizations' ability to reconcile payroll with the actual provider contracts and compensation, produce real-time performance results for providers, and inhibit the transparency between the administration and providers related to the plan's functionality. Disclosed embodiments allow organization leaders to focus more on leading the organization and less on the administrative components of managing provider engagement.

Disclosed embodiments provide techniques for managing several important aspects of provider administration. These include, but are not limited to, compensation plan administration, contract management, provider payment adjudication, market rate identification and fair market value, processing of productivity, quality, and other provider performance data, identification of productivity trends, onboarding of new providers, auto submission of data to Payroll systems, accounts payable and General ledger.

A system in accordance with disclosed embodiments may be implemented using a Software as a Service (SaaS) model, and may be hosted via cloud servers. Staff, providers, and management personnel can thus access the system from a client device remotely. Disclosed embodiments provide a variety of benefits for administration of a provider engagement. Disclosed embodiments can provide a single source for managing the provider compensation process. Furthermore, they allow for transparent, and convenient access to critical data needed to ensure provider compensation aligns with organizational priorities. Yet another feature is ensuring that all payments to providers are consistently calculated and adhere to all contracts between providers and the organization. Yet another feature is to proactively identify providers who are receiving or may receive compensation that may be in excess of the broader market based on various productivity and non-productivity parameters. Embodiments further enable users to identify opportunities for improvement in various metrics that affect provider compensation and performance through the use of intelligent dashboards. Additionally, disclosed embodiments interface with various other systems such as payroll, accounts payable, general ledger, human resources, and legal systems to enable transparency throughout the organization. These and other advantages will be further described in the following description of the figures.

FIG. 1 depicts a system 100 in accordance with embodiments of the present invention. A provider administration system 102 can be implemented in an electronic computing device that includes a processor 140, a memory 142 coupled to the processor, and storage 144, also coupled to the processor 140. Memory 142 contains instructions 147, that when executed by the processor 140, cause the provider administration system 102 to perform steps in accordance with embodiments of the present invention. Memory 142 may be a non-transitory computer readable medium. Memory 142 may include, but is not limited to, flash, read-only memory (ROM), static random-access memory (SRAM), magnetic storage, optical storage, or other suitable storage mechanism. Storage 144 may include one or more magnetic hard disk drives (HDD), solid state disk drives (SSD), optical storage devices, tape drives, and/or other suitable storage devices.

In embodiments, storage 144 may include multiple hard disk drives configured in a RAID (redundant array of independent disks) configuration. In embodiments, the RAID configuration can include a RAID 1 configuration in which data is copied seamlessly and simultaneously, from one disk to another, creating a replica, or mirror. If one hard disk drive becomes inoperable, another hard disk drive continues to operate, providing a level of fault tolerance.

In other embodiments, the RAID configuration can include a RAID 5 configuration in which data and parity are striped across three or more disks. If one hard disk drive within the array gets an error or starts to fail, data is recreated from this distributed data and parity block, seamlessly and automatically. This allows disclosed embodiments to remain operational even when one hard disk drive fails.

In yet other embodiments, the RAID configuration can include a RAID 6 configuration. This configuration is similar to the RAID 5 configuration, with the added enhancement of utilizing more parity blocks than RAID 5, allowing for more hard disk drives to fail while still remaining operational.

In yet other embodiments, the RAID configuration can include a RAID 10 configuration. RAID 10 is a combination of RAID 1 and 0 and is often denoted as RAID 1+0. It combines the mirroring of RAID 1 with the striping of RAID 0, thereby achieving a higher level of performance. Other redundancy schemes are possible with disclosed embodiments.

The processor 140 may include multiple cores. In embodiments, the provider administration system 102 may include multiple processors, where each processor includes multiple cores. Embodiments may schedule tasks and threads over multiple processors and/or cores to achieve a level of parallelism in execution of various tasks such as computations, searching, and/or indexing.

Embodiments may include additional redundancy through failover mechanisms. In embodiments, the provider administration system 102 may be instantiated as a virtual machine operating in a cloud environment. In embodiments, multiple instantiations of the provider administration system 102 may be implemented in the cloud environment. The multiple instantiations may be implemented in geographically diverse datacenters, with data replication and/or other techniques to allow seamless failover from one provider administration system to another provider administration system in the event of a failure at a particular location. In this way, a high level of reliability is achieved.

Provider administration system 102 is in communication with network 124. Network 124 may be the Internet, a local area network (LAN), wide area network (WAN), or another suitable network.

The term "Internet" as used herein refers to a network of networks which uses certain protocols, such as the TCP/IP protocol, and possibly other protocols such as the hypertext transfer protocol (HTTP) for hypertext markup language (HTML) documents that make up the World Wide Web (web). The physical connections of the Internet and the protocols and communication procedures of the Internet are well known to those of skill in the art. Access to the Internet can be provided by Internet service providers (ISP). Users on client systems, such as clients 104 and 106 obtain access to the Internet through the Internet service providers. Access to the Internet allows users of the client computer systems to exchange information, receive and send e-mails, and view documents, such as documents which have been prepared in the HTML format. These documents are often provided by web servers which are considered to be "on" the Internet. Often these web servers are provided by the ISPs, although a computer system can be set up and connected to the Internet without that system being also an ISP as is well known in the art.

One or more client devices, indicated as 104 and 106 may be connected to network 124 via a wired or wireless interface. Clients 104 and 106 may include a mobile computing device such as a smartphone or tablet, a laptop computer, a desktop computer, or other suitable computing device. The client-server architecture allows a user to remotely access features of the provider administration system 102.

Embodiments of the present invention may utilize a JavaScript Object Notation (JSON) web service to make a JSON call to the provider administration system. In some examples, the JSON call is made using XML HTTP, which implements an XML HTTP object that has functionality enabling the exchange of Extensible Markup Language (XML) data directly over the Internet using the Hypertext Transfer Protocol (HTTP). The XML HTTP object allows access of the provider administration system data from a server, parsing the data using an XML Document Object Model (DOM), and posting XML data through a standard firewall directly to an HTTP server.

The provider administration system 102 may be connected to a plurality of networked databases. Once such database may include legal database 160. Legal database 160 may include a corpus of text describing laws, rules, and/or regulations for various jurisdictions. The jurisdictions can include federal, state, county, and local jurisdictions. Another database may include payroll database 162. The payroll database 162 may include payment records for one or more providers that are being tracked within the provider administration system 102.

Another database may include business rules database 164. The business rules database 164 may include various rules for compensation and/or compliance. The compliance rules can be based on Statement on Auditing Standards (SAS) No. 70, Standards for Attestation Engagements (SSAE) No. 16, or other suitable standards. In embodiments, some of the compensation and/or compliance rules may be user-defined.

Another database may include onboarding database 166. The onboarding database 166 may include various fields of tasks that are to be completed/verified at various stages of onboarding to bring a new provider into a medical practice, group or a hospital. These can include licensing and credentialing tasks. Some of these tasks can occur many weeks prior to the new provider's start date. These can include items such as obtaining a state medical license number, a controlled substance certificate, a Medicare number, a Medicaid number, application for hospital privileges, and so on.

The onboarding database may further include tasks pertaining to business administration, such as execution and filing of provider contracts, approvals of various committees, adding the new provider to the schedule, and reviewing various policies with the provider such as the financial policy, fee schedule, social media policy, and the coding and documentation processes used by the practice.

The onboarding database may further include tasks pertaining to human resources, such as completion of federal and state tax forms, completion of mandatory vaccinations, arranging for parking spaces, and so on.

The onboarding database may further include tasks pertaining to IT (information technology), such as setting up email addresses, user accounts, voicemail, building security code access, and so on.

The onboarding database may further include tasks pertaining to marketing, such as ordering of business cards, appointment cards, signage, adding a provider photograph and/or biography to the practice website, and so on. In embodiments, other tasks may be included in the onboarding database instead of, or in addition to, the aforementioned tasks. The Other tasks can be defined per medical group/practice/Hospital's workflow steps that are currently being followed or need to be followed as a process improvement.

Another database may include benchmarking database 166. The benchmarking database 166 may include benchmarking data for one or more benchmarking sources that are being tracked within the provider administration system 102. The benchmarking data may include, but is not limited to, various survey data at local, regional or national level. The survey collects data on practice operational metrics, including hours of operations, wait times, appointments, and no-shows. In embodiments, other metrics may be included instead of, or in addition to, the aforementioned metrics.

Disclosed embodiments may further provide automation and standardization of survey data collection. In traditional administration, collecting the survey data currently is a very disconnected and manual process. Currently, patients receive paper-based survey questions. Health systems and providers that participate in these surveys receive complimentary or discounted fee benchmarking data sets. Disclosed embodiments provide mechanisms to define standard survey parameters and allows survey participants to provide their feedback on quality of services received. This survey data serves as a source for defining benchmarking data.

Disclosed embodiments further enable the use of the collected survey data to derive benchmarking data. In traditional systems, this process currently is done manually. Resultant data is derived by doing several operations such as but not limited to, inflating, applying weightage, and/or blending based upon sample size. Meaningful use of data in a specific specialty group based on survey participants from a certain geographic location is used to derive benchmarking data. Disclosed embodiments automate the entire process by considering data sample size, geographic location and other factors.

Using the information from the aforementioned networked databases and other sources, disclosed embodiments assist in tasks such as provider onboarding and contracts, payroll and provider compensation reconciliation, provider compensation calculations, and provider compensation terms.

Figure 2:
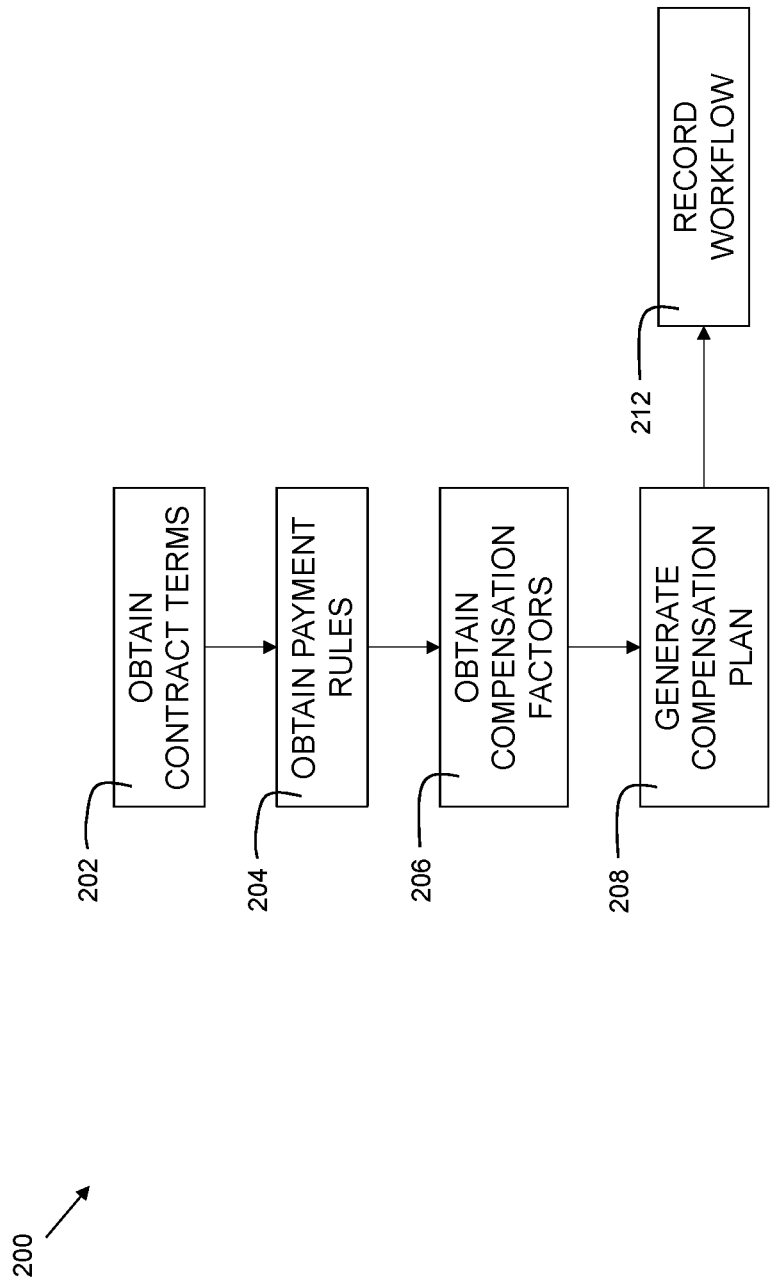
FIG. 2 is a flowchart indicating process steps for embodiments of the present invention.

FIG. 2 is a flowchart 200 indicating process steps for embodiments of the present invention. In process step 202, contract terms are obtained. The contract terms can include a duration, expected duties, and other pertinent information. In process step 204, payment rules are obtained. This can include a compensation model such as salary plus productivity, equal salary, salary plus incentive, or other suitable payment information. In process step 206, compensation factors are obtained. Compensation factors can include, but are not limited to, specialty, experience level, and/or region location. In process step 208, a compensation plan is generated for a provider based on the compensation factors, payment rules, and contract terms. In process step 212 a workflow of pertinent documents is recorded automatically utilizing computer implemented methods, thereby performing workflow automation. The workflow can cover documents such as contract renewals, updates, and/or amendments. This process includes the ability to steer administrators into confirming the availability of hospital privileges, verifying the presence of malpractice insurance, ensuring a provider is set up in the system for billing, and tracking the employment date again future incentives. Embodiments furthermore manage an audit trail of users throughout the on boarding or acquisition process for essential data accessibility and transparency. Thus, embodiments of the present invention can further include performing workflow automation.

Disclosed embodiments enable configuration of provider compensation models/plans intelligently based on various parameters and metrics. This provides an easily configurable approach for creating various provider arrangements and an effective compensation cap (limit).

Additionally, embodiments provide the ability to perform scenario play to identify the best compensation model. Thus, some embodiments further comprise modeling provider compensation utilizing a plurality of compensation models; and providing an indication of compensation plan effectiveness for each model of the plurality of compensation models. The compensation plan effectiveness can be based on how close the projected compensation is to standard compensation based on various factors such as specialty, geographic location, and/or experience level. In embodiments, a plan that results in a provider compensation that is close to (e.g. within five percent) of the average compensation for the given criteria may be deemed as a good plan. In general, establishments often strive to have competitive plans. If compensation is too low, problems of turnover and lack of engagement can occur, and if compensation is too high, it can adversely impact operating costs and/or overall healthcare costs. Therefore, disclosed embodiments improve the technical field of healthcare provider compensation by allowing administrators to execute multiple "what if" scenarios in terms of provider compensation, and rank the various scenarios to guide the administrators to the best scenario for their needs.

In embodiments, compensation plans can be configured based on client, region, location, specialty, provider specific, pay element level information. Disclosed embodiments further provide an "open" ability for clients to run alternative compensation models and scenario play the cause and effect of a potential change on the providers compensation to the provider and administration. Embodiments can further provide a check and balance against the data that has been populated for each providers compensation and steers the administration to accurate and agreed upon compensation model.

Embodiments can further provide a max Compensation or "Hard Ceiling" as a way to ensure there is no overpayment of providers maintaining compliance with the legally agreed upon contract terms and obligation. Disclosed embodiments can prepare providers compensation against performance through alternate models to determine the most effective plan. A variety of types of agreements can be created using disclosed embodiments, including, but not limited to, Call Coverages, Medical Directorships, and/or Private Service Agreements, thereby tactically assisting administration in developing an accurate model for each arrangement.

Standardizing and managing the provider contracts is a time-consuming manual process and lacks the ability to track all activities and communications between various parties involved. Disclosed embodiments provide a single-source system for contracts, exhibits and addendums allowing standardization of provider legal contract management.

Embodiments provide features including, but not limited to, providing alerts and notifications on contract term expiration, thereby delivering consistency to the contract management process. The alerts can be in the form of audio and/or visual alerts such as pop-up messages on a computer screen or mobile electronic device, automatically generated emails and/or text messages, computerized voice messages, and/or other suitable alert mechanism. Embodiments can further include providing an audit trail of users and actions throughout the contract management process for future reference and essential data accessibility and transparency. Embodiments can further provide active management and maintenance of compensation terms (pay elements), thereby steering users to completing time sensitive actions. Embodiments can further provide the administration with techniques for ensuring compliance and the ability to maintain contractual obligations. Embodiments further guide the administration through the approval and payment request process, thereby providing rigor and consistency to the management process. Embodiments can further assist in the transitioning from one compensation model to another, thereby building consistency in the communication and reporting process. Disclosed embodiments can enable the merging of multiple documents and defining the merge order so that provider contracts are one final exhibit. This provides improved convenience for the healthcare administrators. Furthermore, embodiments can generate a completed contractual document for a provider by extracting exhibit language from standard term sheets, templates, and other sources, and automatically populating the terms from the provider profile contained within the system. Thus, embodiments can include generating a completed contractual document for a provider based on template and provider profile information.

Figure 3:
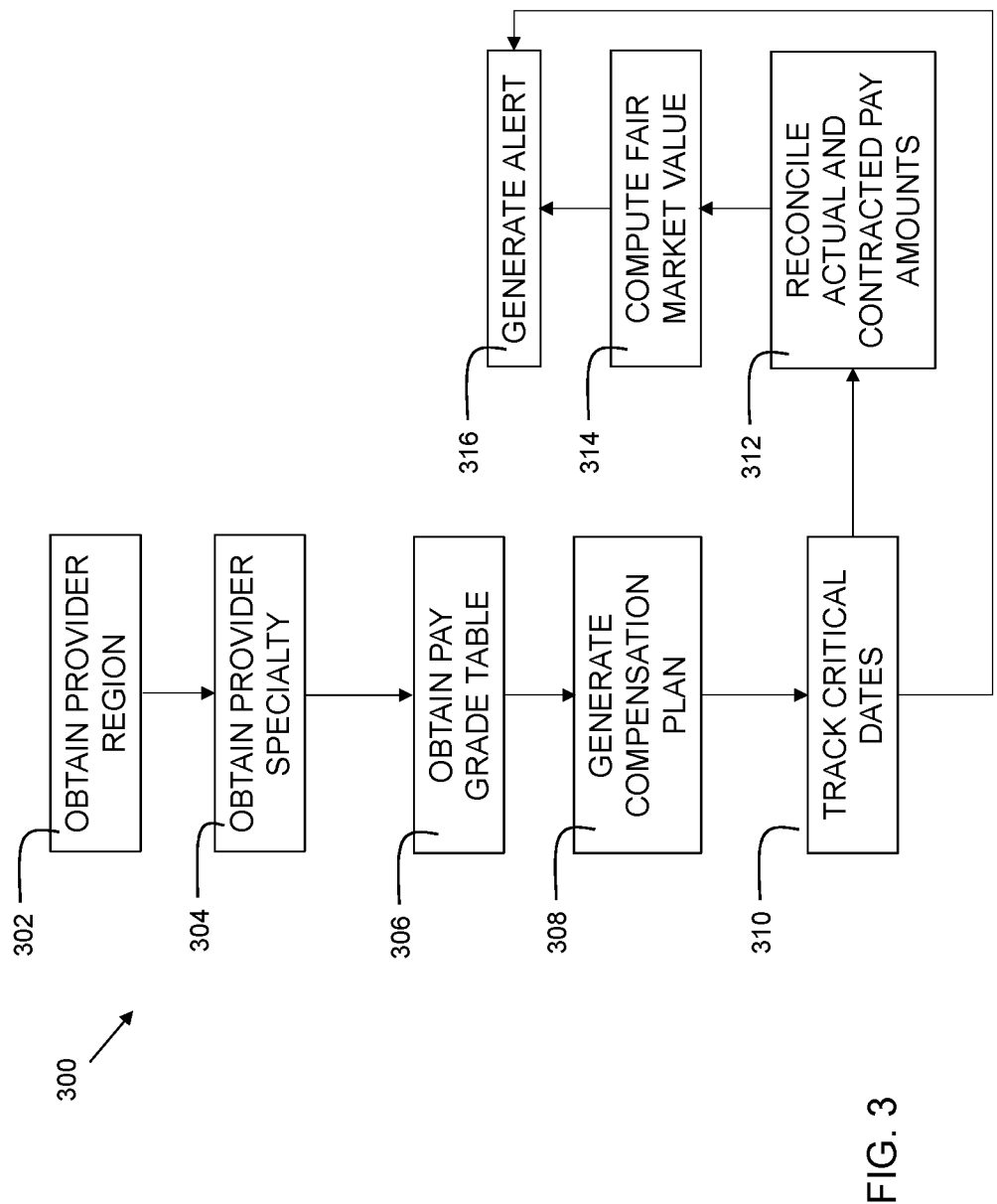
FIG. 3 is a flowchart indicating additional process steps for embodiments of the present invention.

FIG. 3 is a flowchart 300 indicating additional process steps for embodiments of the present invention. In process step 302, a provider region is obtained. The provider region can be a factor in determining provider compensation. The regions can include, but are not limited to, a Mid-Atlantic region, a West region, a Southwest region, a Northeast region, a South-Central region, a Northwest region, a Great Lakes region, and a North Central region. Average salary can differ amongst these regions. Some embodiments may use more or fewer regions. In recent surveys compensation can vary by as much as 30 percent depending on the region. Thus, factoring in the geographic region is an important element in determining an appropriate provider compensation. Disclosed embodiments may apply a correction factor to a proposed provider compensation based on the geographic region.

In process step 304, a provider specialty is obtained. The provider specialty can include, but is not limited to, surgery, radiology, pediatrics, orthopedic surgery, obstetrics/gynecology, internal medicine, otorhinolaryngology, gastroenterology, family medicine, anesthesiology, and/or dermatology. Other embodiments may include more, fewer, and/or different specialty categories. The compensation can vary considerably depending on the specialty. Thus, factoring in the specialty is an important element in determining an appropriate provider compensation.

In process step 306, a provider pay grade table is obtained. The pay grade table may include rates based on experience, years in practice, education level, and/or other factors.

In process step 308, a compensation plan is generated based on the aforementioned factors. The compensation plan can include computation of fixed provider compensation and variable provider compensation. Embodiments configure compensation plans based on client, region, location, specialty, and/or provider-specific pay element level information. This method generates a detailed, accurate, legally compliant, contractually agreed upon compensation model. Disclosed embodiments incorporate contract terms, addendums and renewals, maximum payment rules, key industry measures and standards, client-specific key performance indicators and discreet pay element level details. This provides an ability for clients to run alternative compensation models and execute provider compensation simulations to determine the effect of a potential change on the providers compensation to the provider and administration.

In process step 310, critical dates are tracked. Due dates such as contract expiration, contract Anniversary date, pro ratio date, and/or the payment due date are tracked. In embodiments, at a predetermined time prior to expiry, an alert is generated at process step 316. The alert can be in the form of a text message, email, and/or other suitable alert mechanism to remind a user to take action prior to the expiry of the malpractice insurance. In process step 312, a reconciliation is performed between actual pay amounts (e.g. retrieved from payroll database 162) and contracted pay amounts. Thus, embodiments include reconciling contracted and actual pay amounts.

Another important aspect of provider administration is the upkeep critical dates for things such as contract expiration, contract anniversary dates, payment due dates, and/or the expiry of medical malpractice insurance. Medical malpractice insurance is a specialized type of professional liability insurance that covers provider liability arising from disputed services that result in a patient's injury or death. Medical liability insurance is required in almost all states and most medical systems as a requirement to practice. Malpractice insurance is usually available through traditional insurance carriers or from a medical risk retention group, which is a mutual organization of medical professionals organized to provide liability insurance (sometimes sponsored by state medical societies). Additionally, some large medical systems may be "self-insured;" instead of purchasing commercial insurance, a medical liability trust fund is created that is used to pay for defense of malpractice claims and any resulting judgments against their providers. Thus, upkeep of malpractice insurance is an important part of provider administration. Disclosed embodiments may further assist in management of upkeep of malpractice insurance.

In process step 314 a fair market value (FMV) is computed. Adherence to provider FMV compensation on a recurring basis is critical for meeting compliance requirements and gaining the confidence of the providers. This requires continuous tracking and reconciliation of the actual wages paid against the FMV of provider compensation. Disclosed embodiments provide an electronic warning regarding providers whose compensation is exceeding the benchmarking threshold amount. This is accomplished by comparing their compensation to the benchmarking percentile threshold and/or amount. Disclosed embodiments further provide administration with a consistent method to flag providers that should have an external Fair Market Value assessment completed. Disclosed embodiments further provide tracking and alerts at any user-defined and/or predetermined threshold to allow flexibility for the organization. Disclosed embodiments further provide administration information to evaluate if an external FMV is required based on additional geographical and professional criteria that includes, but is not limited to, specialty, provider group, average by specialty and/or cost center. If the compensation is outside a predetermined range of the contracted pay amount and/or fair market value, a corresponding alert is generated at process step 316.

Figure 4:
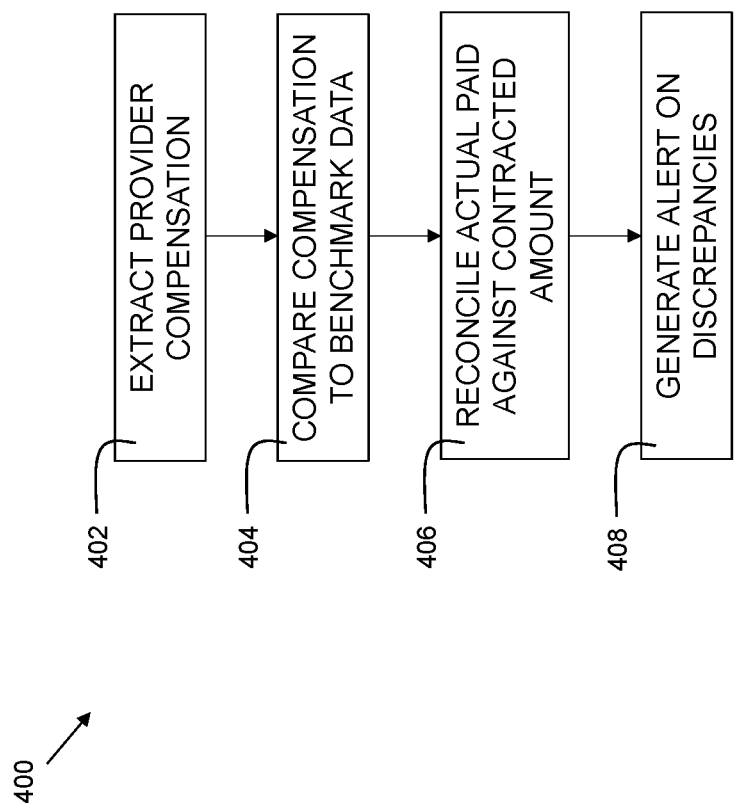
FIG. 4 is a flowchart indicating additional process steps for embodiments of the present invention.

FIG. 4 is a flowchart 400 indicating additional process steps for embodiments of the present invention. In process step 402, provider compensation is extracted. In embodiments, compensation of each provider that is saved in a database accessible by the system is extracted from the exhibits as per the compensation plans.

In process step 404, provider compensation is compared to benchmark data. The benchmarking data may include, but is not limited to, appointment availability, wait times, no-show rates, call volume, turnover, patient satisfaction surveys, provider and employee satisfaction surveys, return visits, and/or other criteria.

In process step 406, provider compensation is reconciled against a contracted amount. Thus, embodiments provide timely tracking and reconciliation of actual compensation paid against contracted compensation wages of providers to ensure providers are compensated as per the fair market value (FMV).

In process step 408, an alert is provided to indicate discrepancies between the actual compensation and the contracted amount to one or more users and/or administrators of the provider administration system. Thus, embodiments can include comparing an actual provider compensation to the calculated fair market value, and generating an alert in response to detecting a discrepancy exceeding a predetermined threshold.

Figure 5:
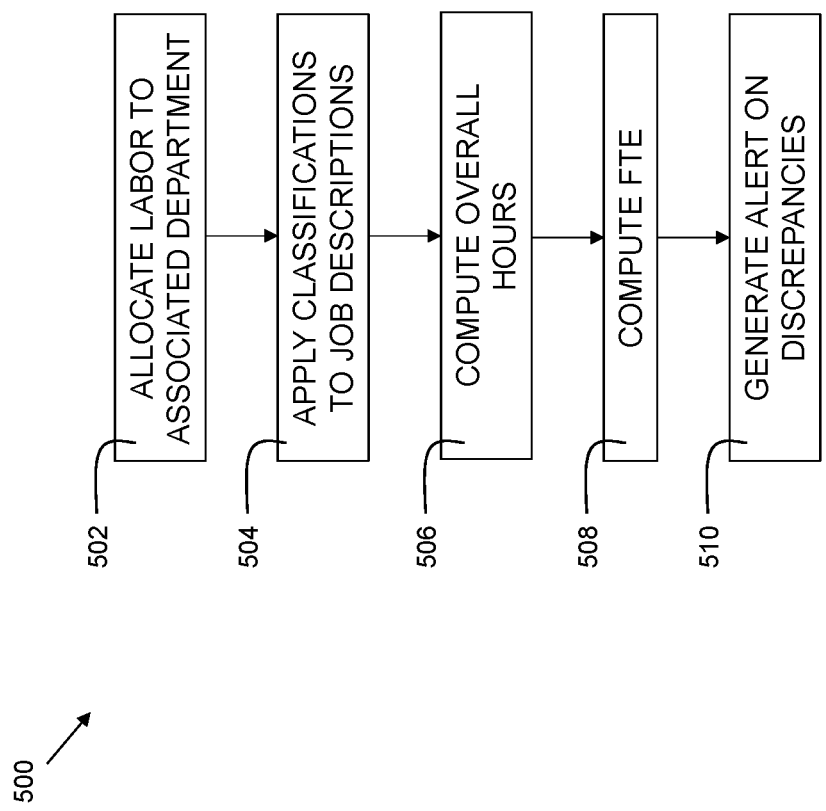
FIG. 5 is a flowchart indicating additional process steps for embodiments of the present invention.

FIG. 5 is a flowchart 500 indicating additional process steps for embodiments of the present invention. In process step 502, labor is allocated to an associated department. In process step 504, classifications are applied to job descriptions. In process step 506, overall hours are computed. In process step 508, Full Time Equivalency (FTE) is computed. In embodiments, an FTE is the hours worked by one employee on a full-time basis. The concept can be used to convert the hours worked by several part-time employees into the hours worked by full-time employees. In embodiments, on an annual basis, an FTE is considered to be 2,080 hours per year. Thus, an FTE can represent the equivalent of one person working full time 8 hours per day, 5 days per week, 52 weeks per year, and/or 2,080 hours/year. In process step 510, an alert is provided to indicate discrepancies in FTE to one or more users and/or administrators of the provider administration system.

Often administrators are required to distribute an individual's FTE value to several departments based on their role and job requirement. Disclosed embodiments provide a labor distribution process. The labor distribution process provides a validation that the value assigned (based on FTE) is consistent with the amount of time spent in each department or on various job responsibilities. Thus, disclosed embodiments provide flexibility in defining FTE classification categories as per a client's requirements. Furthermore, disclosed embodiments provide the ability to assign FTE by category to each provider. Additionally, disclosed embodiments provide assignment of unlimited FTE categories in order to accurately distribute a provider labor (time and role) to the associated department, role or category. These can include, but are not limited to, clinical, teaching, administrative, and/or academic. Disclosed embodiments further provide guidance to an administration in linking the FTE value of a provider against a specific job requirement. This provides further consistency while ensuring accuracy of compensation level against the flexibility of role throughout a day. Embodiments can include comparing a provider full time equivalency (FTE) classification to an actual FTE value, and generating an alert in response to detecting a discrepancy exceeding a predetermined threshold. Furthermore, embodiments can include performing a full-time equivalency (FTE) reconciliation.

Figure 6:
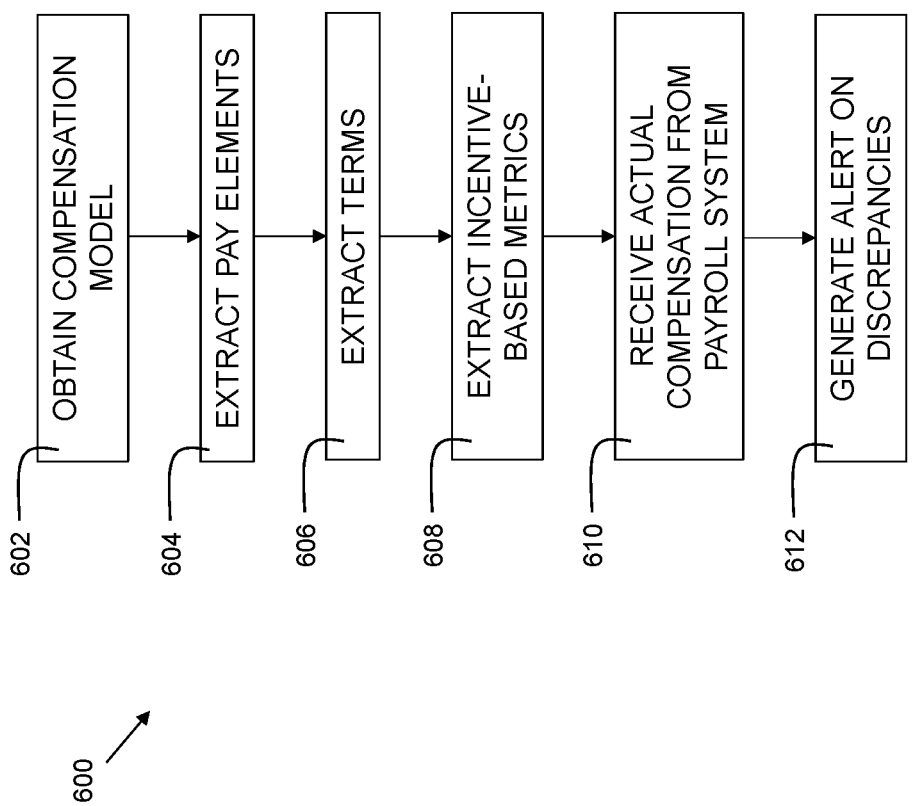
FIG. 6 is a flowchart indicating additional process steps for embodiments of the present invention.

FIG. 6 is a flowchart 600 indicating additional process steps for embodiments of the present invention. In process step 602, a compensation model is obtained. In embodiments, the compensation model can include but not limited to a straight salary model, guaranteed salary model, salary plus bonus/incentive model, collections model, and/or a productivity-based compensation model. In process step 604, pay elements are extracted. Pay elements can include a variety of additional factors used in determining provider compensation. Pay elements can include, but are not limited to, base salary, call coverage pay, holiday pay, medical directorship pay, meeting pay, relocation pay, supervision pay, productivity bonus, performance bonus, and/or training pay. In process step 606, terms are extracted. The terms can include rates and/or amounts for compensation for the various pay elements. In process step 608, incentive-based metrics are extracted. In process step 610, actual compensation is retrieved from the payroll system/database and/or accounts payable system/database. In process step 612, an alert is provided to indicate discrepancies in compensation to one or more users and/or administrators of the provider administration system.

Provider compensation reconciliation between contracted terms and actual payroll is very challenging due to the two being disparate systems, and involves various complex parameters. This process in the industry is performed manually using spreadsheets that leads to several discrepancies. Disclosed embodiments provide a systematic way of calculating and reconciling contracted wages as compared with actual wages. Disclosed embodiments enable complete reconciliation of the contract and payroll as the solution collects, stores and manages contracts, compensation models, pay elements and all incentive based metrics. Disclosed techniques can provide an efficient and automated way to reconcile and record any discrepancies that exists between compensation derived from contractual terms and what was paid to the provider. Embodiments generate a payroll alert against any variance that requires action. Disclosed embodiments further provide reconciliation between the compensation that is calculated by the system against the generated payroll by referring to the contractual terms established for a provider. Disclosed embodiments guide the reduction of discrepancies that can exists with disparate systems and manual processes. Furthermore, disclosed embodiments guide the administration in producing an accurate, contractually compliant payroll. Additionally, disclosed embodiments provide an electronic alert for variance violations between compensation calculated and compensation paid. Disclosed embodiments further provide a mechanism for importation of a file from payroll/accounts payable to deliver a level of rigor and consistency to the adjudication process, thereby ensuring accuracy and compliance.

Figure 7:
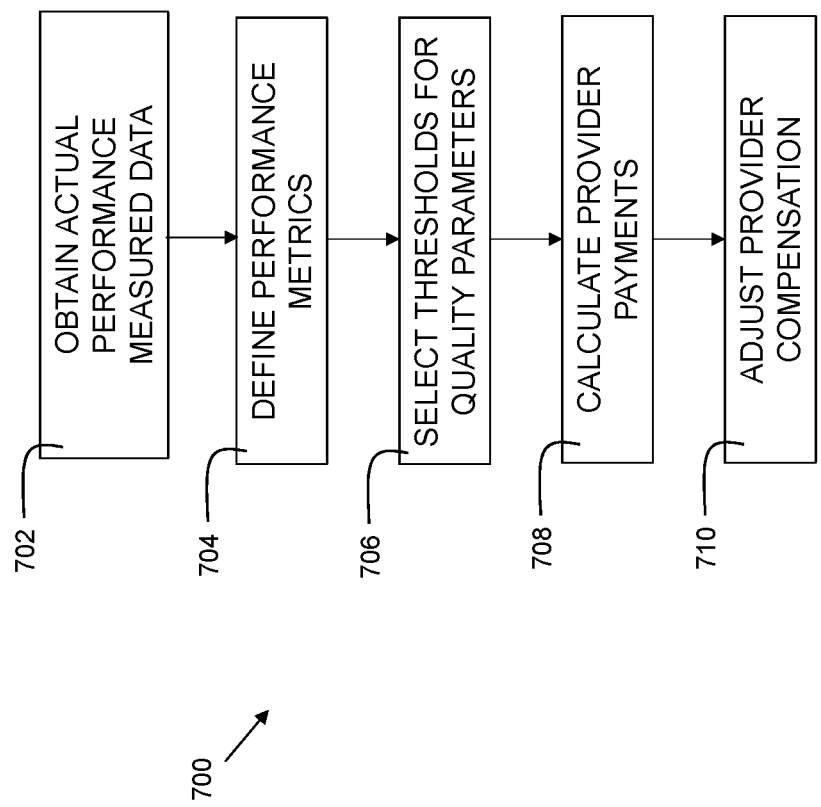
FIG. 7 is a flowchart indicating additional process steps for embodiments of the present invention.

FIG. 7 is a flowchart indicating additional process steps for embodiments of the present invention. In process step 702, actual performance measured data is obtained. The performance measured data can include, but is not limited to, FTE classification categories, benchmarking comparison and blending by specialty, and/or quality component and its impact on compensation. The FTE classification categories can include, for a given provider, an FTE rating, a clinical earnings value, a non-clinical earnings value, and/or an administrative earnings value.

The benchmarking comparison and blending by specialty can include a comparison of various parameters. These parameters can include compensation, wRVU, collections, a ratio of compensation to collections, compensation per wRVU, and/or collections per wRVU. The benchmarking comparison can include a comparison of the aforementioned parameters by specialty, provider, and/or other criteria. Specialties can include, but are not limited to, internal medicine, neurological surgery, obstetrics/gynecology, cardiology, orthopedic surgery, dentistry, and/or dermatology, among others.

The quality component can include, but is not limited to, a bonus type, a contractual FTE value, a bonus amount paid, a bonus determination formula, a tier range met, a total number of measures, and/or a max bonus opportunity. Embodiments can include identifying incentive metrics and measures, setting of thresholds, establishing of a payment methodology (compensation plan) and/or completion of compensation calculations. Disclosed embodiments, through pulling client specific data, provides the ability to calculate and reconcile against the calculation against the pre-determined range. The range is used to determine the percentage with which the compensation is calculated and then FTE adjusted.

In process step 704, performance metrics are defined. In embodiments, the performance metrics may be defined by provider specialty and/or cost center. In process step 706, thresholds are selected for quality parameters. These parameters may be used to measure the quality of work against various external industry standard data sets and metrics, such as, for example, the Healthcare Effectiveness Data and Information Set (HEDIS). HEDIS which is a set of performance metrics developed and maintained by the National Committee for Quality Assurance (NCQA). The metrics include parameters pertaining to high-cost conditions such as heart disease, diabetes, high blood pressure, as well as preventive measures like immunizations and medication management. In process step 708, provider payments are calculated based on assessed quality metrics. In process step 710, provider compensation is adjusted as per the calculated provider payments.

FIG. 8 is an exemplary user interface 800 in accordance with embodiments of the present invention. In embodiments, this user interface 800 is rendered on a client device (e.g. 104 and/or 106 of FIG. 1). The user interface may be rendered via an application executing on the client device. Alternatively, the user interface may be a browser-based user interface implemented via one or more HTML pages. Other suitable user interface implementations are possible. Multiple data fields may be present on user interface 800. As shown in FIG. 8, user interface 800 includes a provider name field 802, a contract duration field 806, and a specialty field 804.

User interface 800 may further included a projected RVU field 808. A relative value unit is applied to the various Current Procedural Terminology® (CPT) codes used to describe and bill professional services. RVU computation can include work, practice expense, malpractice, and/or other aspects. User interface 800 may further include a projected collections field 810. This can include projected collections based on provider activities. User interface 800 may further include one or more pay elements 812. Each pay element may be implemented as a checkbox or other suitable user interface. As can be seen in FIG. 8, some pay elements are selected (checked) while others are unselected (unchecked). For example, the Base Salary pay element is checked, while the Moonlighting Pay element is unchecked. Pay elements can include, but are not limited to, Base Salary, Call Coverage Pay, Draw Against Productivity, Hard to Fill Incentive Pay, Holiday Pay, Hospitalist Pay, Medical Directorship Pay, Meeting Pay, Moonlighting Pay, Relocation Pay, Sign on Bonus Pay, Slow Shift Pay, Straight Productivity, Supervision Pay, and Training Pay. Embodiments may include more, fewer, and/or different sets of pay elements. The information entered into user interface 800 can be used to rapidly administer a compensation plan. Each of the pay elements can be a factor in determining an expected and/or actual compensation for a provider.

As can now be appreciated, disclosed embodiments provide techniques that alleviate the challenges healthcare leaders face in the administration and management of provider compensation. Disclosed embodiments provide systems and methods that automate calculating and adjudicating, and monitoring provider compensation while providing real-time feedback to administrators and providers on performance under the compensation methodology. The automation allows organizations to increase transparency while providing secure access to information, allowing for more robust discussion of alternatives and alignment between the enterprise users and providers. Thus, disclosed embodiments serve to ensure compliance, enable transparency, and empower validation throughout the provider compensation process.

Additionally, disclosed embodiments provide a complete, end-to-end system for compensation management, evaluation, calculation and adjudication. Disclosed embodiments capture essential information from the acquisition/onboarding process through calculating of payroll and adjudicating with the payroll solution. Disclosed embodiments allow for file uploads and downloads and automated interfaces with other disparate systems leveraged during compensation management. Disclosed embodiments allow each user access to any authorized, essential data from the same source information that the entire organization is leveraging.

Disclosed embodiments process practice management data in a consistent, transparent manner to enable actionable intelligence to the applicable user groups within an organization. This solution provides automation and consistency to the rules that are applied to the practice management data before it is utilized for bonus calculation purposes. This solution further provides a mechanism to capture several other data points, including, but not limited to, Current Procedural Terminology (CPT) codes, patient level data (if required), payroll information, human resources data, and/or benchmarking in "role-based" functionality.

Additionally, disclosed embodiments provide dashboards, time collection, pay requests, productivity monitoring, paid time off, and continuing medical education (CME) tracking in a real-time user experience. Embodiments can guide data manage to deliver a consistent compilation and reporting of compensation information. Furthermore, disclosed embodiments provide demographic information to track critical information allowing supporting documentation to be accurate and consistent with what is contractually obligated. Thus, disclosed embodiments provide a single solution for managing provider administration. Therefore, disclosed embodiments include generating a compensation plan that includes providing compensation data serving as a single data source.

While aforementioned examples described compensation and administration for a provider, disclosed embodiments can be applied to other non-provider personnel, including, but not limited to, nurse practitioners, nurses, technicians, and other specialists.

The present invention may be a system, a method, and/or a computer program product at any possible technical detail level of integration. The computer program product may include a non-transitory computer readable storage medium (or media) having computer readable program instructions thereon for causing a processor to carry out aspects of the present invention.

Each of the above methods may be executed on one or more processors on one or more computer systems. Embodiments may include various forms of distributed computing, client/server computing, and cloud based computing. Further, it will be understood that the depicted steps or boxes contained in the disclosed flowcharts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Any and all such functions, generally referred to herein as a "circuit," "module," or "system" may be implemented by computer program instructions, by special-purpose hardware-based computer systems, by combinations of special purpose hardware and computer instructions, by combinations of general purpose hardware and computer instructions, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Program data may also be received via the network adapter or network interface.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

It will be appreciated that computer program instructions may include computer executable code. A variety of languages for expressing computer program instructions may include without limitation C, C++, Java, JavaScript™, assembly language, Perl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Furthermore, the method steps shown are intended to include any suitable method of causing one or more parties or entities to perform the steps.

The terminology used herein is for describing particular aspects only and is not intended to be limiting of the invention. As used herein, the singular forms "a", "an" and "the" are intended to include the plural forms as well, unless the context clearly indicates otherwise. It will be further understood that the terms "include" and "including" when used in this specification, specify the presence of stated features, integers, steps, operations, elements, and/or components, but do not preclude the presence or addition of one or more other features, integers, steps, operations, elements, components, and/or groups thereof. Certain examples and elements described in the present specification, including in the claims and as illustrated in the figures, may be distinguished or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations or process steps.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method executed by a system for healthcare provider compensation management and administration, the system comprising:
   a virtual machine operating in a cloud environment,
      wherein the instantiation is implemented in geographically diverse datacenters with data replication to allow failover from one provider administration system to another provider administration system in an event of a failure at a particular location, and
   wherein the system is programmed via instructions to perform the following steps of the computer implemented method:
      obtaining contract terms for use in a contact with a healthcare provider as a first step;
      obtaining payment rules as a second step;
      obtaining compensation factors as a third step;
      generating a compensation plan for the healthcare provider based on the obtained contract terms, payment rules, and compensation factors as a fourth step
      generating a contract for the healthcare provider's services based on the first, second, third, and fourth steps;
      automating a workflow of documents pertaining to the first, second, third, and fourth steps, and the contract, including automatically recording the documents used in those steps and the contract;
      tracking contract addendums and renewals;
      incorporating information of the contract terms, addendums, and renewals, maximum payment rules, discreet pay element details, and at least one of a measure, a standard, and a performance indicator, to assess services provided by the healthcare provider, and to determine a plurality of alternative compensation models and, using those models, to execute fora user of the system a plurality of provider compensation simulations to determine the effect of at least one contemplated change in the provider's compensation plan;
      providing updates to information of actual service performance in real time;
      calculating a fair market value (FMV) of the services provided by the provider over a time period ending at a current time, thereby providing a real time user experience, wherein calculation of the FMV includes assessment of geographical criteria and professional criteria comprising at least a FMV of a specialty associated with the provider and a FMV of a providergroup associated with the provider;
      accessing at least a legal database and a payroll database, each being connected to the provider compensation management and administration system, to ensure compliance with legally agreed upon contract terms and obligations,
         wherein the legal database comprises a corpus of text describing laws, rules, and/or regulations for jurisdictions,
         wherein the jurisdictions comprise federal jurisdictions, state jurisdictions, county jurisdictions, and local jurisdictions, and
         wherein the payroll database comprises payment records for one or more providers that are being tracked within the provider compensation management and administration system;
      reconciling, using at least the legal database and the payroll database, the provider's actual compensation for services provided over a time period for which the provider has been compensated, with the provider's contracted compensation over that time period and the fair market value of the services provided over that time period; and
      in the event the difference between the actual compensation and the reconciled amount exceeds a predetermined threshold, sending an alert message to the provider and an administrator of the provider compensation management and administration system.

2. The method of claim 1, wherein obtaining compensation factors includes obtaining a provider region.

3. The method of claim 1, wherein obtaining compensation factors includes obtaining a provider specialty.

4. The method of claim 1, wherein obtaining compensation factors includes obtaining a provider pay grade table.

5. The method of claim 1, further comprising computation of fixed provider compensation and variable provider compensation.

6. The method of claim 1, further comprising performing a full-time equivalency (FTE) reconciliation.

7. The method of claim 1, further comprising reconciling contracted and actual pay amounts.

8. The method of claim 1, further comprising performing a calculation of fair market value.

9. The method of claim 1, further comprising adjusting provider compensation based on comparison of performance measured data with industry-standard data sets.

10. The method of claim 9, wherein the performance measured data includes one or more FTE classification categories.

11. The method of claim 9, wherein the performance measured data includes a benchmarking comparison.

12. The method of claim 9, wherein the performance measured data includes a quality component.

13. The method of claim 1, wherein generating a compensation plan further comprises incorporating, maximum payment rules, key industry measures and standards, client-specific key performance indicators and discreet pay element level details.

14. The method of claim 8, further comprising:
comparing a provider compensation to the calculated fair market value; and
generating an alert in response to detecting a discrepancy exceeding a predetermined threshold.

15. The method of claim 9, further comprising generating a completed contractual document for a provider based on template and provider profile information.

16. The method of claim 1, further comprising performing workflow automation.

17. The method of claim 1, further comprising:
modeling provider compensation utilizing a plurality of compensation models; and
providing an indication of compensation plan effectiveness for each model of the plurality of compensation models.

18. The method of claim 1, wherein generating a compensation plan includes providing compensation data serving as a single data source.

19. The method of claim 1, further comprising automating survey data collection.

20. The method of claim 19, further comprising using survey data to derive benchmarking data.

* * * * *